(12) United States Patent
Rao et al.

(10) Patent No.: US 7,725,330 B2
(45) Date of Patent: May 25, 2010

(54) SYSTEMS AND METHODS FOR AUTOMATED EXTRACTION AND PROCESSING OF BILLING INFORMATION IN PATIENT RECORDS

(75) Inventors: R. Bharat Rao, Berwyn, PA (US); Radu Stefan Niculescu, Pittsburgh, PA (US); Sathyakama Sandilya, Malvern, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 685 days.

(21) Appl. No.: 10/727,197

(22) Filed: Dec. 3, 2003

(65) Prior Publication Data

US 2004/0172297 A1    Sep. 2, 2004

Related U.S. Application Data

(60) Provisional application No. 60/430,428, filed on Dec. 3, 2002.

(51) Int. Cl.
*A61B 5/00*     (2006.01)

(52) U.S. Cl. ..................... 705/3; 705/4; 705/2

(58) Field of Classification Search .......... 705/2–4
See application file for complete search history.

(56) References Cited

U.S. PATENT DOCUMENTS

| | | | |
|---|---|---|---|
| 5,253,164 A | 10/1993 | Holloway et al. | |
| 5,307,262 A | 4/1994 | Ertel | |
| 5,359,509 A | 10/1994 | Little et al. | |
| 5,544,044 A | 8/1996 | Leatherman | |
| 5,664,109 A | 9/1997 | Johnson et al. | |
| 5,772,585 A * | 6/1998 | Lavin et al. | 600/300 |
| 5,809,476 A | 9/1998 | Ryan | |
| 5,832,447 A * | 11/1998 | Rieker et al. | 705/2 |
| 5,933,809 A * | 8/1999 | Hunt et al. | 705/3 |
| 6,182,029 B1 * | 1/2001 | Friedman | 704/9 |
| 6,341,265 B1 * | 1/2002 | Provost et al. | 705/4 |
| 6,343,271 B1 * | 1/2002 | Peterson et al. | 705/4 |
| 6,347,329 B1 * | 2/2002 | Evans | 709/202 |

(Continued)

FOREIGN PATENT DOCUMENTS

JP    7160770 A    6/1995

(Continued)

OTHER PUBLICATIONS

Managed Care: New Financial /Practice Strategies to Manage More Efficiently /Effectively in a Primary Care Setting (Virginia Smith Harvin, Michael O Martin, Gustavo Gallego.Nursing Administration Quarterly. Frederick :Spring 1998; vol. 22, Iss.3; pp. 1-5).*

(Continued)

*Primary Examiner*—Vanel Frenel
(74) *Attorney, Agent, or Firm*—Joshua B. Ryan

(57) ABSTRACT

Systems and methods for automated processing of medical information in electronic patient medical record databases, wherein billing information (e.g., diagnosis codes, procedural codes) is automatically extracted from electronic patient medical records through comprehensive analysis of clinical information included in the patient medical records using a knowledge base of domain-specific criteria. The extracted billing information can be automatically processed for purposes of, e.g., medical claims correction, medical claims billing, quality assurance of recorded billing information, or claim reimbursement tracking.

31 Claims, 8 Drawing Sheets

U.S. PATENT DOCUMENTS

| | | | |
|---|---|---|---|
| 6,529,876 B1 | 3/2003 | Dart et al. | |
| 6,770,029 B2* | 8/2004 | Iliff | 600/300 |
| 6,915,254 B1 | 7/2005 | Heinze et al. | |
| 7,440,904 B2 | 10/2008 | Hasan et al. | |
| 2004/0172291 A1 | 9/2004 | Rao et al. | |

FOREIGN PATENT DOCUMENTS

| | | |
|---|---|---|
| JP | 2001175724 A | 6/2001 |
| JP | 2002288336 A | 10/2002 |

OTHER PUBLICATIONS iMedica Creates the Most Comprehensive Charting Solution Harnessing the Power of the Internet Wirelessly ; (PR Newswire; New York; Jan 18, 2000; pp. 1-3.*

Lernout & Haustie: Lernout & Haustie strengthens medica offerings in Europe; acquires assets of CAMS (M2 Presswire; Coventry; Aug. 31, 1999; pp. 1-4.*

(Managed Care: New Financial/ Practices Strategies to Manage More Efficient /Effectively in a Primary Care Setting by Virginia Smith Harvin; 1998.*

(iMedica Creates the Most Comprehensive Charting Solution Harnessing the Power of the Internet Wirelessly by PR Newswire, N.Y Jan. 18, 2000).*

Heinze, Daniel et al: "LifeCode—A Deployed Application for Automated Medical Coding", AI Magazine, American Association for Artificial Intelligence, [Online], vol. 22, No. 2, Jun. 2001, retrieved from the Internet: URL:http://www.alifemedical.com/documents/LifeCodeAIMagazine.pdf>.

Heinze, Daniel et al. "LifeCode—A Deployed Application for Automated Medical Coding", AI Magazine, American Association for Artificial Intelligence, [Online], vol. 22, No. 2, Jun. 2001, retrieved from the internet: URL: http://www.alifemedical.com/documents/LifeCodeAIMagazine,pdf>.

* cited by examiner

Criteria For Diagnosis of AMI:
A Four-way Classification at Three Levels

| Cardiac Pain | YES | | | NO |
|---|---|---|---|---|
| EKG Change | Classic Change With evolution | Static Change from an old EKG | Atypical findings on EKG | Normal |
| Enzyme Change | Unequivocally Abnormal | Equivocal Abnormalities | | Normal |
| Definite MI | Probable MI | Possible MI | | No MI |
| Diagnosis of Acute MI | | | | |

FIG. 4A

Criteria for Enzymes

| Enzyme | Abnormal | Equivocal | Normal |
|---|---|---|---|
| TROPONIN (Code TROP) | TROP >3.0 | TROP >1.5 but <3.0 | WNL ($\leq 1.5$) |
| TOTALCPK (Code: CPK or TCPK) CK-MB (Code MBCPK) ... | IF TCPK/CPK >200, THEN CKMBRI >10.0<br><br>IF TCPK $\leq$200, THEN MBCPK >7.0 | IF TCPK/CPK >200, THEN CKMBRI >5.0 but <10<br><br>IF TCPK $\leq$200, THEN MBCPK >3 but <7 | IF TCPK/CPK >200, CKMBRI<5.0<br><br>IF TCPK <200, THEN MBCPK <3 |
| Domain Knowledge for diagnosing abnormal enzyme levels | | | |

FIG. 4B

SYSTEMS AND METHODS FOR AUTOMATED EXTRACTION AND PROCESSING OF BILLING INFORMATION IN PATIENT RECORDS

CROSS-REFERENCE TO RELATED APPLICATION

This application claims priority to U.S. Provisional Application Ser. No. 60/430,428, filed on Dec. 3, 2002, which is fully incorporated by reference.

TECHNICAL FIELD OF THE INVENTION

The present invention generally relates to systems and methods for automated processing of medical information in electronic patient medical record databases. More specifically, the invention relates to systems and methods for automatically extracting billing information (e.g., diagnosis codes, procedural codes) from electronic patient medical records through comprehensive analysis of clinical information included in the patient medical records using a medical knowledge base of domain-specific criteria, as well as systems and methods for automated processing of extracted billing information for purposes of, e.g., medical claims correction, medical claims billing, quality assurance of recorded billing information, or claim reimbursement tracking.

BACKGROUND

Due to continued technological advancements in data storage systems and information processing systems, health care providers and organizations continue to migrate toward environments where most aspects of patient care management are automated, making it easier to collect and analyze patient information. Consequently, health care providers and organizations, etc., tend to accumulate vast stores of patient information, such as financial and clinical information, in electronic patient medical records in electronic databases. Health care organizations, however, typically maintain clinical information in a myriad of unstructured and structured formats, which may contain missing, incorrect, and inconsistent data.

One source of error or inconsistency for patient data stored in a database is due to the improper codification or classification of particular medical diagnoses and procedures in the form of standardized "Codes". Various types of standardized coding systems have been developed as nationally accepted common formats for numerically specifying, e.g., medical conditions/diagnoses or medical services/resources. For instance, clinical data may be classified according to specific cases or medical conditions (or a group of diagnoses and conditions) using codes that follow the International Classification of Diseases (ICD) standard. In particular, ICD Codes include, for example, the International Classification of Diseases, Ninth Revision, Clinical Modification (ICD-9-CM), which is based on the World Health Organization's Ninth Revision, International Classification of Diseases (ICD-9). ICD-9-CM is an official system of assigning codes to diagnosis and procedures associated with hospital utilization in the United States. The Tenth Revision (ICD-10) has been released, which is expected to be implemented soon. Other types of standardized coding systems include, for example, CPT (current procedural terminology) codes, HCPCS (health care procedure coding system) codes, DRG (diagnosis related group) codes and APC codes.

There are various factors that can contribute to the improper classification of patient clinical information using standardized Codes. For instance, the coding process can be viewed as a two-step mental process that includes (i) assessing/diagnosing a medical condition/disease based on, e.g., a patient's symptoms and (ii) assigning a Code (e.g., ICD code) to the medical condition/disease. Accordingly, the coding process is subjective to some extent, since the codification process can be performed by a variety of people who possess different skills and expertise, which can result in different assessments of a medical condition and/or codification of such assessments. For example, different doctors (e.g., surgeon, internist) may select different ICD codes to specify a diagnosis of a particular medical condition of a patient based on, the actual condition of a particular organ of the patient, or the symptomatic status of the patient.

Moreover, for some conditions, the coding system may not have sufficient data options to accurately reflect the condition. In addition, codes can be incorrectly input in electronic medical records of a patient as a result of human error. As a result, the diagnosis codes that are included in electronic patient medical records of a clinical database can inaccurately represent the actual medical condition of the patients.

The "Codes" that are included in patient medical records for classifying medical conditions and procedures can be used for various purposes, such as sources of information for clinical data analysis, as well as sources of data for electronic systems for insurance claims and medical billing. Therefore, it is important to properly codify medical conditions and services so that medical billings and insurance claim analyses will accurately reflect the actual medical conditions of the patient and medical services rendered. Indeed, inaccurate code assignments for medical conditions and services can result in inappropriate reimbursement for medical claims by insurance companies, as well as rejection or partial payment of medical claims.

SUMMARY OF THE INVENTION

Exemplary embodiments of the invention generally include systems and methods for automated processing of medical information in electronic patient medical record databases. Exemplary embodiments of the invention include systems and methods for automatically extracting billing information from patient medical records through comprehensive analysis of clinical information in the patient medical records using domain-specific criteria from a domain knowledge base.

In particular, in one exemplary embodiment of the invention, a method for processing medical information includes the steps of obtaining a medical record of a patient, wherein the medical record comprises patient information from one or more structured and unstructured data sources, and automatically extracting billing information from the medical record by analyzing the patient information in the medical record using domain-specific criteria. In one embodiment, the billing information includes one or more billing codes comprising diagnosis codes and/or procedure codes.

In another exemplary embodiment of the invention, the process of extracting billing information comprises extracting all possible billing codes that are supported by the patient information based on all domain-specific criteria in a domain knowledge base. The domain-specific criteria comprise condition-specific or disease-specific domain knowledge and possibly institution-specific domain knowledge and clinical guidelines.

Furthermore, in other exemplary embodiments of the invention, automated systems and methods are provided for automatically processing billing information (e.g., diagnosis codes and procedural codes) extracted from medical records. More specifically, in one exemplary embodiment, systems and methods are provided for automatically correcting and updating patient medical records in a medical database using billing information that is extracted from the medical records, with or without user verification. For instance, a patient medical record can be corrected or updated by deleting incorrect codes that are recorded in the patient medical record, replacing incorrect codes that are recorded in the patient record with correct codes, or by including extracted billing codes that are not recorded in the patient record (missing codes), but which are supported by the clinical data, etc.

In yet other exemplary embodiments of the invention, systems and methods are provided for automatically generating medical claims for purposes of billing using billing information that is extracted from patient medical records, with or without user verification.

In other exemplary embodiments of the invention, systems and methods are provided for providing automated quality assurance of billing information in a database of patient medical records. For example, exemplary systems and methods are provided for automatically generating and reporting statistics with respect to the quality of data as recorded in a billing database by comparing extracted billing codes from patient records in the billing database against actual recorded billing codes in the medical records and assessing the quality of billing information in the billing database based on the number or frequency of occurrence of correctly recorded billing codes, incorrectly recorded billing codes, or missing billing codes (i.e., billing codes that are not recorded although supported by patient information in the patient records).

In yet other exemplary embodiments of the invention, systems and methods are provided for automatically tracking medical claims reimbursements. For instance, in one exemplary embodiment of the invention, expected reimbursements can be automatically determined based on billing information recorded in medical patient records, and received reimbursements can be automatically tracked against the expected reimbursements for purposes or automated medical claims accounting.

These and other exemplary embodiments, aspects, features and advantages of the present invention will become apparent from the following detailed description of exemplary embodiments, which is to be read in connection with the accompanying drawings.

BRIEF DESCRIPTION OF THE DRAWINGS

FIGS. 4A and 4B are exemplary diagrams illustrating domain-specific criteria of a domain knowledge base, which can be used as for extracting and processing billing information in an electronic patient medical record according to an exemplary embodiment of the invention.

DETAILED DESCRIPTION OF EXEMPLARY EMBODIMENTS

Exemplary embodiments of the invention generally include systems and methods for automated processing of medical information in electronic patient medical record databases. More specifically, exemplary embodiments of the invention include systems and methods for automatically extracting billing information from patient medical records through comprehensive analysis of clinical information in the patient medical records using domain-specific criteria of a medical knowledge base. Furthermore, exemplary embodiments of the invention include systems and methods for automated processing of extracted billing information for purposes of generating medical claims, correcting/updating billing information in medical record databases, or providing quality assurance of billing information in medical records databases, etc.

It is to be understood that the systems and methods described herein in accordance with the present invention may be implemented in various forms of hardware, software, firmware, special purpose processors, or a combination thereof. In one exemplary embodiment of the invention, the systems and methods described herein are implemented in software as an application comprising program instructions that are tangibly embodied on one or more program storage devices (e.g., hard disk, magnetic floppy disk, RAM, CD Rom, DVD, ROM and flash memory), and executable by any device or machine comprising suitable architecture.

It is to be further understood that because the constituent system modules and method steps depicted in the accompanying Figures can be implemented in software, the actual connections between the system components (or the flow of the process steps) may differ depending upon the manner in which the application is programmed. Given the teachings herein, one of ordinary skill in the related art will be able to contemplate these and similar implementations or configurations of the present invention.

Figure 1:
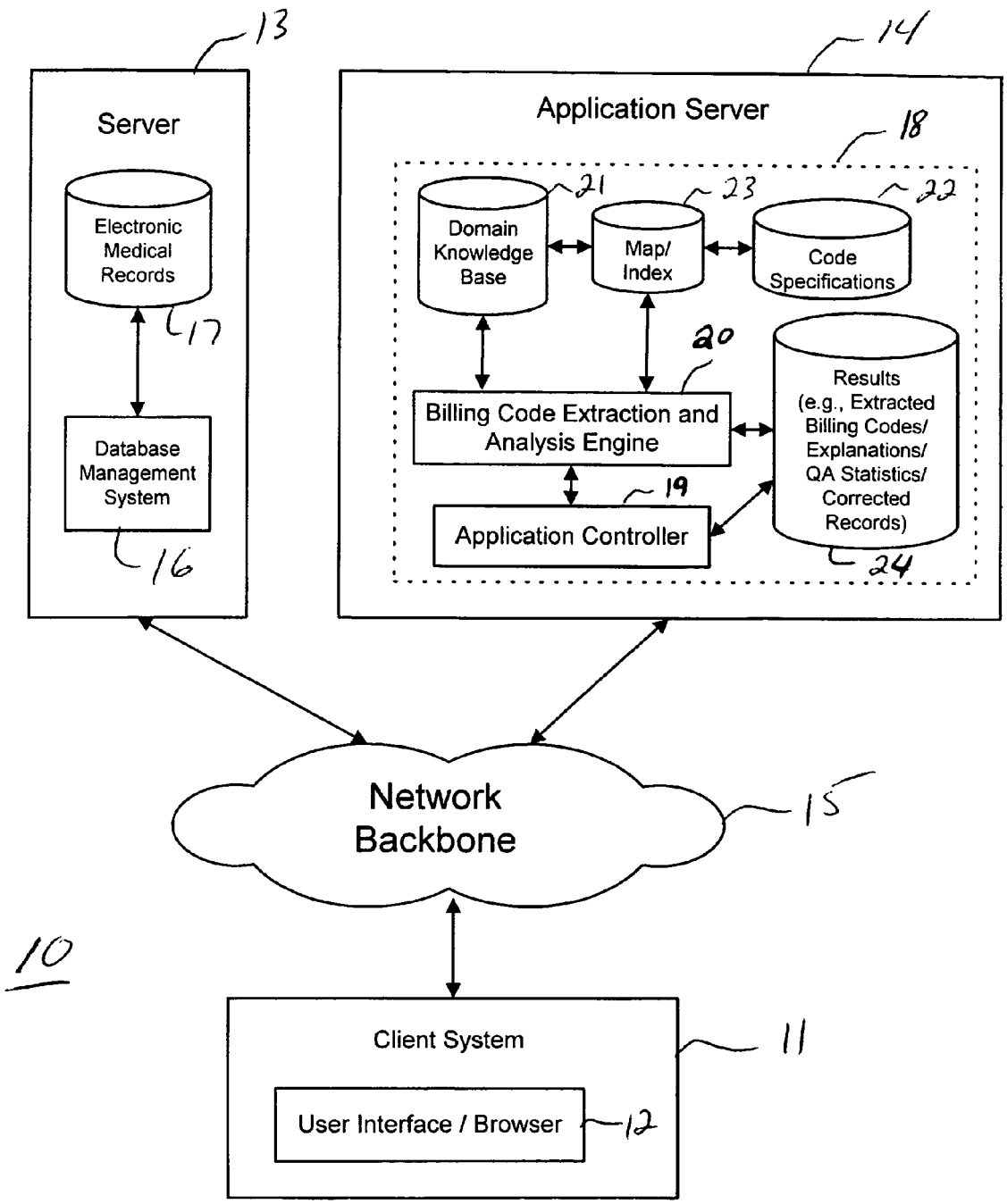
FIG. 1 illustrates a system for automated extraction and processing of billing information in a database of patient medical records, according to an exemplary embodiment of the invention.

Referring now to FIG. 1, a high-level schematic diagram illustrates a medical information processing system (10) according to an exemplary embodiment of the invention. More specifically, FIG. 1 illustrates a system (10), which can be implemented by health care providers, institutions, associations, organizations, hospitals, etc., for automated extraction and processing of billing information contained in databases/repositories of patient medical records. In general, the system (10) comprises a client system (11), such as a computer workstation, personal computer, portable computing device, etc., that executes a client application (12) (e.g., client browser) to provide a user interface for accessing a database server (13) and an application server (14) via network connections over communications network (15). In particular, by way of example, the client system (11) may comprise a user workstation having I/O devices such as a display, mouse, keyboard, etc., for supporting a GUI interface, or a wireless handheld device (e.g., PDA, laptop, etc.) having I/O modalities for supporting a speech interface, GUI interface, or combination speech/GUI interface.

The server (13) comprises a database management system (16) for managing an electronic database (17) of patient data, and handling access requests for patient data. In general, in one exemplary embodiment of the invention, the database (17) comprises a repository of individualized patient data in the form of computerized patient records (CPR) (or electronic patient medical records) for one or more patients.

Figure 2:
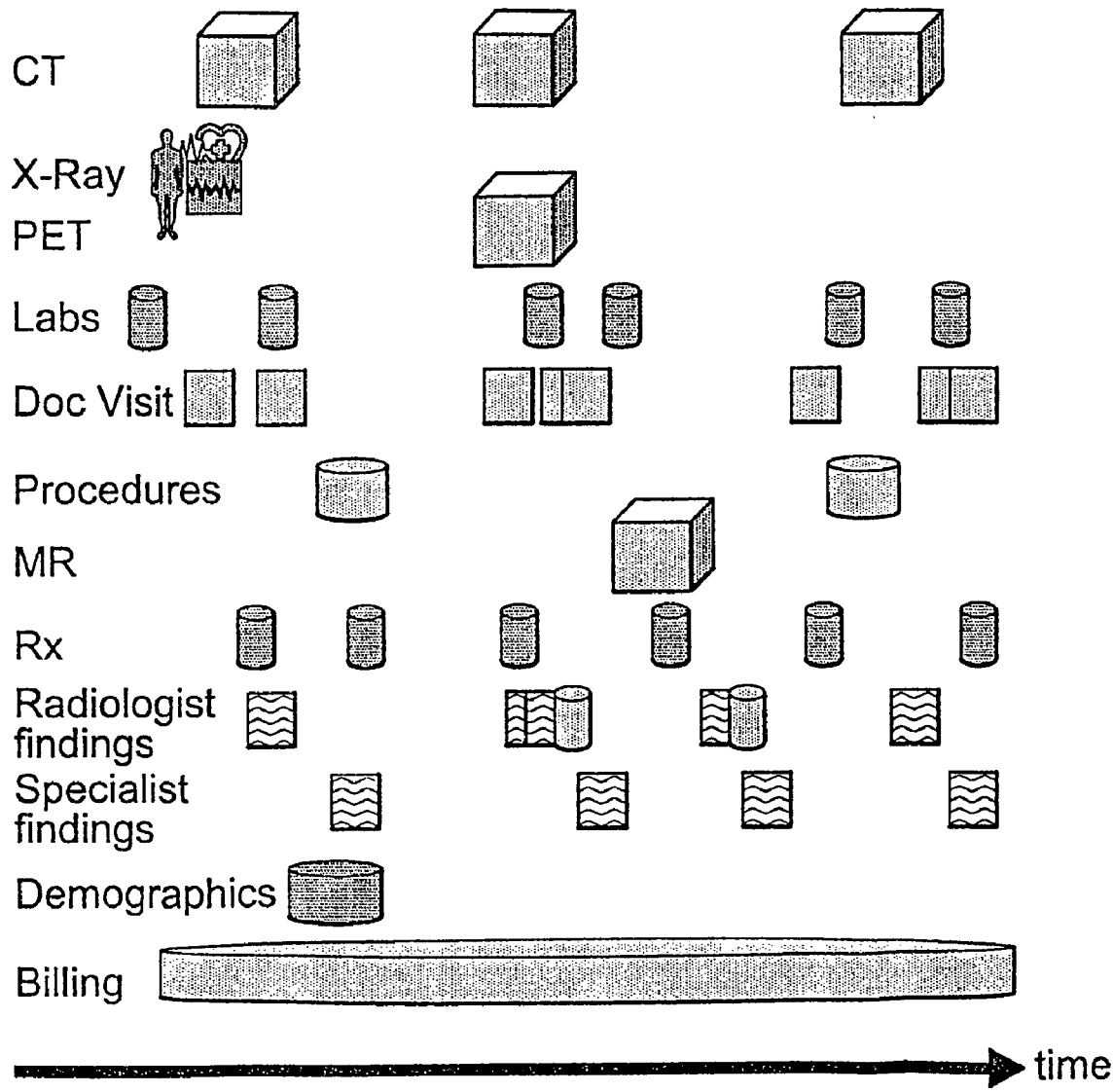
FIG. 2 illustrates an exemplary electronic patient medical record comprising a plurality of structured and unstructured data sources from which billing information can be automatically extracted and processed using systems and methods according to exemplary embodiments of the invention.

For example, FIG. 2 illustrates an exemplary electronic patient medical record (25) comprising patient data that is collected over the course of a patient's treatment. More specifically, the exemplary CPR (25) comprises a plurality of structured and unstructured data sources for maintaining patient information, wherein each data source reflects a different aspect of a patient's care. The patient information may include, e.g., computed tomography (CT) images, X-ray images, laboratory test results, doctor progress notes, details about medical procedures, prescription drug information, radiological reports, other specialist reports, demographic information, and billing (financial) information. In general, the structured data sources include, for example, financial, laboratory, and pharmacy databases, wherein patient information in typically maintained in database tables. The unstructured data sources include for example, free-text based documents (e.g., physician reports, etc.) and images and waveforms data. Often, key clinical findings are only stored within physician reports.

Various data sources (e.g., billing/insurance databases, or other structured patient data sources) of the electronic medical record (25) of a patient can include standardized Codes that are used to identify medical treatments, medical procedures, and/or medical diagnoses (of medical conditions/diseases) of the patient. Moreover, the medical record may contain patient information from unstructured sources (e.g., physician's notes) including, for example, written statements of particular medical diagnoses or medical procedures. For reasons as noted above, such Codes or conclusions/assertions may incorrectly reflect a patient's actual medical condition. Furthermore, there may be codes that are not included (missing information) in the patient financial information of billing/insurance databases, which should be included based on diagnosis an procedures that are supported based on patient clinical data. Accordingly, systems and methods according to the invention can be implemented to provide automated procedures for extracting and processing billing information in patient records for purposes of updating/correcting medical claims and enabling quality assurance of financial information for purposes of proper claim submission and reimbursement, as well as other procedures as described herein.

Referring again to FIG. 1, in accordance with an exemplary embodiment of the invention, the application server (14) hosts an application (18) that can be accessed for providing automated extraction and processing of billing information from electronic patient medical records stored in database (17). The application server (14) includes methods for dispatching pages and/or code/scripts (e.g., Applets, JavaScript, etc.) to the client system (11) over a network connection, which is processed by the client application (12) for rendering a user interface (e.g., GUI windows) for interacting with the application (18). The user interface enables a user to submit queries, commands, data, etc., to the server (14) for processing by the application (18). The application server (14) further comprises code for dispatching processing results to the client system (11), wherein the processing results are rendered by the client application (12).

It is to be understood that although a client-server framework is depicted FIG. 1, the system (10) may be implemented using any suitable computing environment framework such as P2P (peer-to-peer) or master/slave, for example. The network (15) may comprise any suitable network configuration such as an Intranet, a LAN (local area network), WAN (wide area network), P2P, a global computer network (e.g., Internet), a wireless communications network, a virtual private network (VPN), etc.

In another embodiment of the invention, the application (18) can be a service (e.g., Web service). For example, several hospitals may participate in the service to have their patient information analyzed for quality assurance, and other purposes as described herein, for example, and this information may be collectively stored in a data repository (e.g., the data repository (24), FIG. 1) maintained by the service provider. The service may be performed by a third party service provider (i.e., an entity not associated with the hospitals).

Moreover, in another embodiment of the invention, the entire system (10) can be implemented on a single, standalone computer system. Those of ordinary skill in the art can readily envision various architectures for implementing the system (10) and nothing herein shall be construed as a limitation of the scope of the invention.

In the exemplary embodiment depicted in FIG. 1, the application (18) comprises an application controller (19) (or dialog manager), a billing code extraction and analysis engine (20), and a plurality of persistent storage repositories for maintaining various data including, for example, a domain knowledge base (21), code specifications (22), a map/index data structure (23), and processing results (24).

The application controller (19) processes user queries/commands/data, etc., received via the user interface (12) of the client system (11), and controls execution of the application (18).

The domain knowledge base (21) comprises, e.g., domain-specific knowledge for diagnosing one or more medical conditions, diseases, etc. In particular, in one exemplary embodiment of the invention, each medical diagnosis (or "domain-specific condition") is defined using domain-specific criteria, wherein the domain-specific criteria for a given medical diagnosis comprise a description of one or more clinical criterion that provide the basis for establishing such medical diagnosis (e.g., diagnosing a specific medical condition or disease, etc.). Furthermore, the domain knowledge base (21) comprises domain-specific criteria for various domain-specific medical procedures/resources, which enable the engine (20) to extract/identify/analyze patient information related to medical procedures, resources, etc. In one exemplary embodiment of the invention, the domain-specific criteria are primarily disease/condition-specific, but may contain some hospital specific information, or may contain clinical guidelines, for example.

By way of example, FIGS. 4A and 4B illustrate domain-specific criteria, in the form of table data structures, which are used for diagnosing acute myocardial infarction (AMI). In the exemplary embodiment, the diagnosis of AMI depends on the unequivocal presence or absence of a combination of three factors: (i) symptoms of cardiac pain; (ii) changes in EKG (electrocardiogram); and (iii) change in enzymes that are released by injured heart muscle. FIG. 4B illustrates domain-specific criteria for diagnosing abnormal enzyme levels.

Assuming an individual had cardiac pain, the degrees to which changes in EKG and enzymes meet the criteria, individually and in combination, determine the certainty of the diagnosis ("definite", "probable", or "possible").

By way of further example, domain-specific criteria for diagnosing diabetes can be based on clinical data regarding pharmacy records in hospital showing (i) administration of drugs administered to the patient that are associated with the treatment of diabetes such as Insulin or Oral agents specific to diabetes; and/or (ii) patient's lab records having values that are diagnostic of diabetes (e.g., 2 random blood sugars above 300 mg/dl).

Moreover, the knowledge base may comprise domain-specific criteria for procedural codes. For instance, knowledge regarding a plurality of medical procedures related to heart disease, such as angioplasty, can be specified using domain-specific criteria for identifying relevant patient information associated with such procedures.

Referring again to FIG. 1, the code specifications repository (22) stores Codes that are associated with one or more coding systems supported by the application (18) for codifying medical diagnoses (medical conditions, diseases, etc.), such as ICD codes, etc., as well as coding systems for codifying medical procedures/resources, such as CPT codes, etc. Each medical diagnosis (domain-specific condition) and medical procedure/resource specified in the knowledge base (21) is logically associated to one more diagnosis codes/procedural codes of the relevant coding system(s) in the code specification repository (22) using, for example, an indexing or mapping mechanism. For example, the map/index repository (23) comprises a map/index data structure that maps, or otherwise indexes, each domain-specific condition or medical procedure (defined in the domain knowledge base (21)) to relevant Codes in each of the supported coding systems that are maintained in the code specifications repository (22).

In general, the engine (20) uses the domain-specific criteria (or is configured using the domain-specific criteria) to extract and analyze information from patient medical records. More specifically, the engine (20) comprises methods for analyzing patient clinical information within a patient medical record from various data sources (structured and unstructured) using domain-specific criteria in the domain knowledge base (21) to automatically extract billing information (e.g., diagnosis codes, procedural codes) from the patient medical record.

In particular, in one embodiment, the engine (20) will analyze the patient clinical information in the medical records using all the domain-specific criteria that is specified in the knowledge base (21) for medical diagnoses and procedures, to thereby determine every possible medical diagnosis and procedure that is supported by the patient clinical information to some specified degree of certainty. Preferably, this analysis is performed without reference to, or without placing any significant weight on, the Codes that are actually included/recorded in the patient medical record (e.g., in a structured billing record). For each medical diagnosis and procedure that the engine (20) determines to be supported by the clinical information in the patient medical record, the engine (20) can determine the corresponding diagnosis codes and procedural codes via the map/index (23). The result of such automated analysis is an extraction of all billing information supported by the clinical information of the patient medical record. The results can be stored in the repository (24) for subsequent access for one of various applications as described herein, such as automated medical billing, quality assurance, etc. In other exemplary embodiments of the invention, depending on the application, the engine (20) can perform an automated extraction process for one or more "target" diagnoses or procedures that are specified in a user query/command, for example, without having to analyze the patient medical record for all medical diagnoses and procedures specified in the domain knowledge base (21).

It is to be appreciated that the application (18) can be configured to operate in one or more modes, thereby enabling the system (10) to be implemented in various applications for automated processing of extracted billing information. For instance, as described below with reference to FIG. 5, in one mode of operation, the engine (20) can automatically correct and update one or more patient medical records in a medical database using billing information that is extracted from the medical records, wherein the automatic correcting and updating of patient records can be performed with or without user verification. For instance, as explained in further detail below, the engine (20) can correct a patient medical record by deleting incorrect codes that are recorded in a patient medical record, replacing incorrect codes that are recorded in a patient record with correct codes, or update a record by including codes that are not recorded in the patient record (missing codes), but which are supported by the clinical data, etc. The results of such automated process are corrected/updated claims/records that can be stored in repository (24).

Furthermore, in another exemplary embodiment as described below with reference to FIG. 6, in another mode of operation, the engine (20) can automatically generate medical claims for purposes of billing using the extracted billing information, wherein the automatic medical claims generation can be performed with or without user verification. In another exemplary embodiment, the application (18) may be a tool or component that is used for extracting billing information to input to a separate automated medical claims billing system.

Moreover, in yet another exemplary embodiment of the invention as described below with reference to FIG. 7, in another mode of operation, the engine (20) can be implemented for providing automated quality assurance of billing information in a database of patient medical records. For example, the engine (20) can be configured for generating statistics with respect to the quality of data as recorded in billing information databases. More specifically, in one exemplary embodiment, for each patient medical record in a database, the engine (20) can reconcile the extracted billing codes against the actually recorded billing codes and collecting information regarding the accuracy of manual assessment and recording of billing codes in the database by determining the number of times codes were correctly recorded, incorrectly recorded, or missed (i.e., not recorded although the clinical data supports such billing codes). The quality assurance results and statistics can be maintained in the repository (24).

Furthermore, in yet another exemplary embodiment of the invention as described below with reference to FIG. 8, in another mode of operation, the engine (20) can be implemented for tracking medical claims reimbursements. In particular, the engine (20) can extract billing information from a medical patient record, or it can extract actual recorded billing information that is known to be correct, and automatically determine the amount of expected reimbursement for a medical claim based on the actual billing information. The expected reimbursement can be reconciled against actual reimbursements to determine and track surpluses or losses resulting from medical claims.

It is to be appreciated than any suitable data analysis/data mining technique may be implemented in the engine (20) for extracting and analyzing clinical information from electronic medical records. In one exemplary embodiment of the invention, the engine (20) is implemented using the systems and methods described in commonly assigned and copending U.S. patent application Ser. No. 10/287,055, filed on Nov. 4, 2002, entitled "Patient Data Mining", which claims priority to U.S. Provisional Application Ser. No. 60/335,542, filed on Nov. 2, 2001, which are both fully incorporated herein by reference. For example, FIG. 3 illustrates a system and method for extracting and analyzing patient information included in an electronic medical record, as disclosed in the above-incorporated application.

Figure 3:
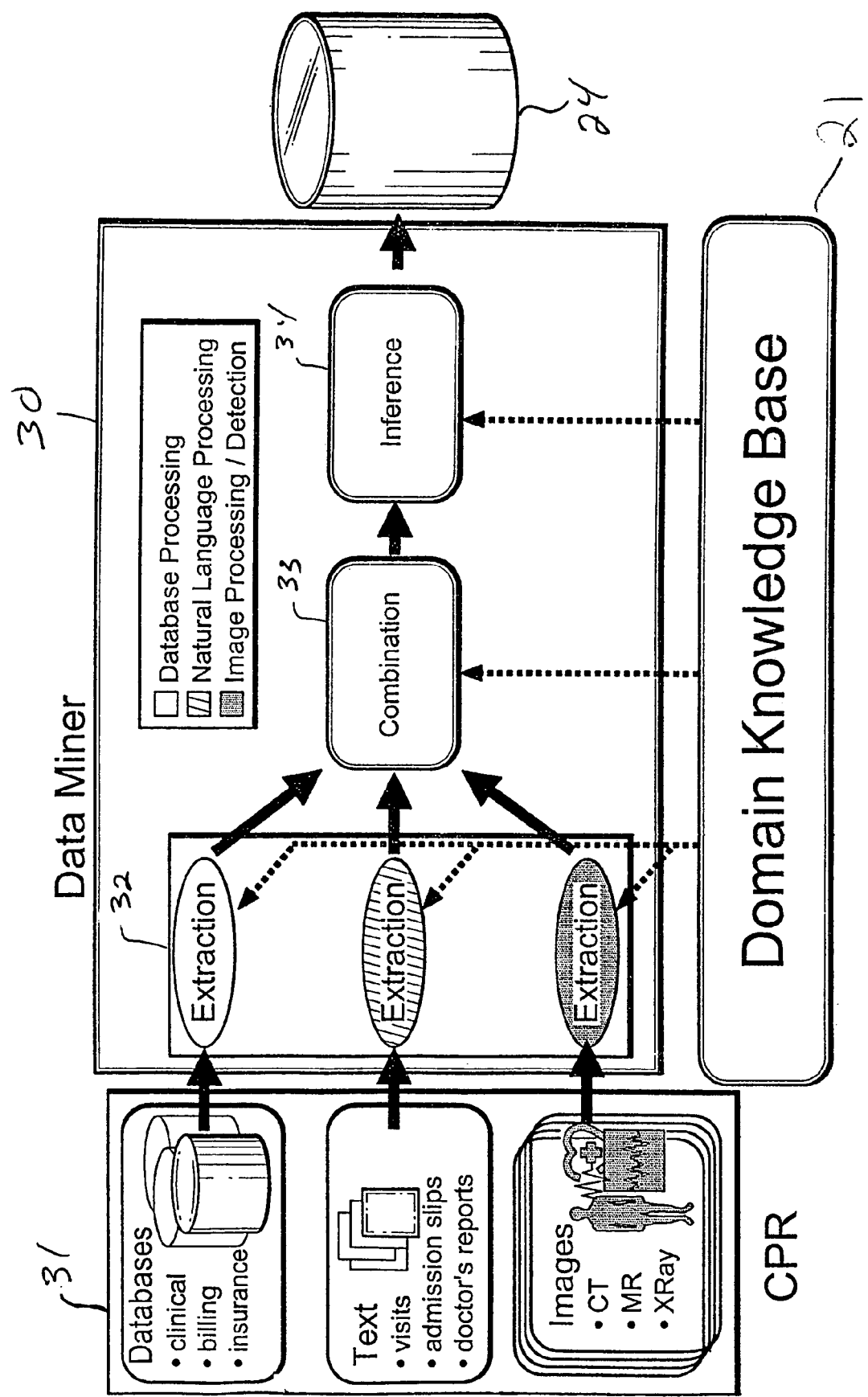
FIG. 3 illustrates details of an exemplary system that can be implemented for automatically extracting and processing billing information from electronic patient medical records, according to an exemplary embodiment of the invention.

Referring to FIG. 3, a data mining system includes a data miner (30) that extracts information from a CPR (31) using domain-specific knowledge contained in a knowledge base (21). The data miner (30) includes various modules/components for extracting information from the CPR (31), combining all available evidence in a principled fashion over time, and drawing inferences from such combination process. More specifically, an extraction module (32) includes methods for extracting small pieces of information from each of a plurality of data sources (database, text, images) of patient data within the CPR (31), which are represented as probabilistic assertions about the patient at a particular time. These probabilistic assertions are called elements. A combination module (33) combines all the elements that refer to the same variable (domain-specific criteria) at the same time period to form a single unified probabilistic assertion regarding that variable. These unified probabilistic assertions are called factoids. An inference module (34) analyzes the factoids, at the same point in time and/or at different points in time, to produce a coherent and concise picture of the progression of the patient's state over time. This progression of the patient's state is called a state sequence. In accordance with the present invention, the inference module (34) can determine a probability of the existence of a particular condition based on an analysis of the extracted clinical information using domain-specific criteria.

Indeed, each module (32, 33, and 34) uses detailed knowledge (domain-specific criteria) regarding the particular domain-specific condition (medical diagnosis) in question. The domain knowledge base (21) can be encoded as an input to the system, or as programs that produce information that can be understood by the system. The domain knowledge base (21) may also be learned from data. The domain-specific knowledge may include disease-specific domain knowledge, such as discussed above with reference to FIGS. 4A and 4B. For example, the disease-specific domain knowledge may include various factors that influence risk of a disease, disease progression information, complications information, outcomes and variables related to a disease, measurements related to a disease, and policies and guidelines established by medical bodies. The domain-specific knowledge may also include institution-specific domain knowledge. For example, this may include information about the data available at a particular hospital, document structures at a hospital, policies of a hospital, guidelines of a hospital, and any variations of a hospital.

As noted above, a system for providing automated extraction and processing of billing information in patient records according to an exemplary embodiment of the invention can be configured for providing a plurality of operational modes that enable automated extraction and processing of billing information for various applications. Various operational modes for automated processing of billing information according to exemplary embodiments of the invention will now be discussed in detail with reference to the flow diagrams of FIGS. 5-8, for example.

Figure 5:
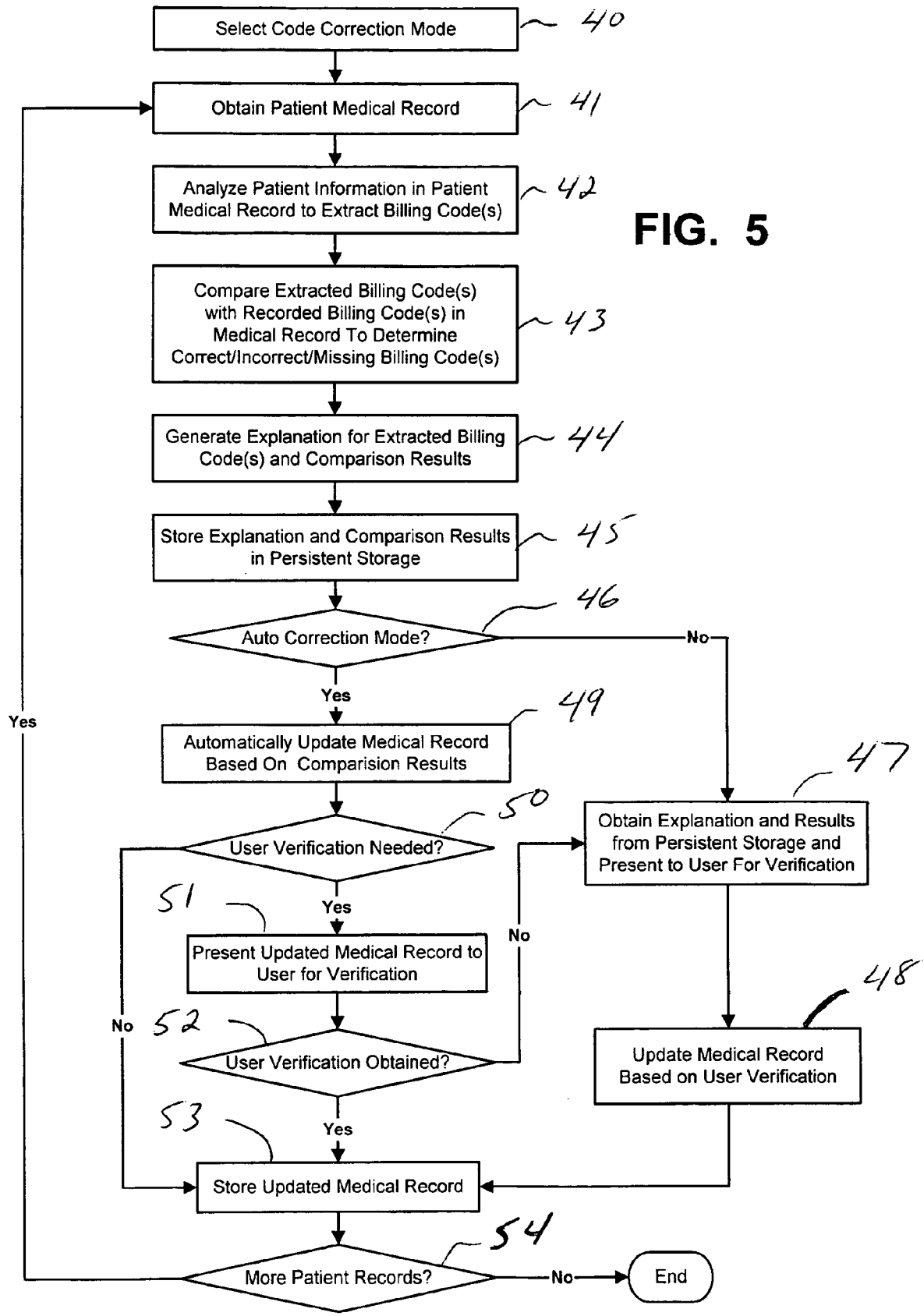
FIG. 5 is a flow diagram of a method for automatically extracting and processing billing information in patient medical records according to an exemplary embodiment of the invention.

Referring to FIG. 5, a flow diagram illustrates a method for automatically extracting and processing billing information in patient medical records for providing automated or semi-automated code correction according to exemplary embodiments of the invention. Initially, a user (e.g., health care professional) wanting to verify the correctness of billing codes (diagnosis and procedural code) in a repository of patient medical records, can access an automated code extraction and analysis system/application configured for performing such task, such as described above with reference to FIG. 1, for example. In one embodiment of the invention such as depicted in FIG. 1, the system resides on a remote server over a network, in which case the user connects to the server via a secure network connection using a suitable client device and performs an authorization procedure (password, speaker identification, etc.) to login to the system. As noted above, the system may comprise a Web service offered by a third-party under a contract or service level agreement for providing, e.g., secured automated extraction and analysis of billing information associated with patient records.

When the user is granted authorized access to the system, the client will render a user interface that enables the user to interact with the system in one or more supported modalities (e.g., GUI and/or speech interface). For instance, in one exemplary embodiment of the invention, the user can begin interaction by selecting a mode of operation of the system for billing code correction (step 40). The user can submit a suitable query or command, which is received and processed by the system to commence processing of all patient medical records in a particular database and the system will begin accessing the patient medical record(s) (e.g., CPR) in accordance with the user query/command (step 41). For example, in one embodiment of the invention, the system can directly access/obtain such patient medical record(s) from a location (e.g., URI, URL, directory, or other pointer, etc.) specified in the query/command submitted by the user. In another exemplary embodiment of the invention, the user can actually transmit (via a secured network connection) a copy of the patient records/files using any suitable compression, encryption, and/or communication protocols.

For each patient medical record that is accessed (step 41), the system will automatically extract one or more billing codes from the medical record by analyzing the patient information in the medical record using domain-specific criteria (step 42). In particular, in one exemplary embodiment of the invention, the process of extracting billing information comprises extracting all possible billing codes (including diagnosis codes and procedural codes) that are supported by the patient clinical information in the medical based on all domain-specific criteria in a domain knowledge base. When performing automated extraction of billing information, the system does not consider or give significant weight to actual diagnosis codes or procedural codes recorded in the patient record as supporting evidence for billing information, since the validity of these recorded codes is what is being determined. However, depending on the domain-specific criteria, other codes related to medical procedures, resources, etc., may be defined as criteria for establishing a particular diagnosis. As noted above, the extraction and analysis of the clinical information can be performed using the data extraction and analysis methods of the above-incorporated patent application, Ser. No. 10/287,054 (FIG. 3).

Next, the system will identify (or otherwise extract) the billing code(s) that are actually recorded in the patient medical record and compare the recorded billing code(s) with the extracted billing code(s) to determine whether the recorded billing codes are "correct" or "incorrect" and/or determine if the patient medical record is "missing" a billing code(s) that should be included (sep 43). More specifically, in one exemplary embodiment, a recorded billing code will be deemed "correct" and accepted if there is a corresponding extracted billing code based on the patient information (e.g., clinical information). Indeed, in such instance, the recorded billing code will be deemed acceptable as being supported by the patient information in the medical record based on relevant domain-specific criteria for such for such billing code. In addition, a recorded billing code will be deemed "incorrect" and rejected, if there is an extracted billing code that is contrary to the recorded billing code. Indeed, in such instance, the recorded billing code will be deemed unacceptable as not being supported by patient information in the medical record. Furthermore, a billing code will be deemed "missing", if the recorded billing codes in the patient medical record do not include an extracted billing code. Indeed, in such instance, the billing code is deemed missing as being supported by the patient information, but yet not included in the medical patient record. The results of the comparison (in step 43) include an indication as to the actual recorded billing codes that are "correct" or "incorrect", as well as an indication as to billing codes that are "missing" and should be included in the patient medical record.

Next, the system can generate an explanation for the extracted billing information, which can include the comparison results (step 44) and store the explanation and comparison results persistently for subsequent access (as explained below) (step 45). More specifically, in one exemplary embodiment, an explanation includes one or more pointers to relevant patient information, relevant domain-specific criteria, or relevant patient information and domain-specific criteria, which supports the extracted billing information. The explanation may further comprise information as to whether or not clinical guidelines have been followed as specified by domain-specific criteria. As explained below, the explanation can be present to a user for verifying the billing information and results of comparison.

In one embodiment of the invention, an explanation can be generated and presented using the methods described in commonly assigned U.S. patent application Ser. No. 10/287,075, filed on Nov. 4, 2002, entitled "Patient Data Mining, Presentation, Exploration and Verification", which is fully incorporated herein by reference. This application discloses a system and method for generating a graphical user interface for presenting, exploring and verifying patient information. A method is provide which enables browsing mined patient information, such as selecting patient information to view and presenting the selected patient information on a screen, wherein the selected patient information includes links to related information. The selected patient information may include raw information extracted from various data sources for the patient (referred to as 'elements') or conclusions drawn there from. The selected patient information may include an element linked to unstructured information. For example, an element linked to a note with highlighted information may be presented. The highlighted information may refer to information used to derive the element. Additionally, the unstructured information may include medical images and waveform information. The selected patient information may also be derived from structured data sources, such as a database table. The selected patient information may include a document with links to elements associated with the document. Further, the selected patient information may include patient summary information.

The code correction mode may include an "Auto Correction" mode, in which the system automatically corrects or updates the patient medical records, either with or without user verification. If the system is not operating in Auto Correction mode (negative determination in step 46), upon user request, the system can obtain the corresponding explanation and comparison results from storage and present the explanation and comparison results to the user for verification (step 47). In such case, the user can view the extracted billing information, the supporting evidence for the extracted billing information, and the possible corrections/updates that can be made to the medical record of the patient as indicated by the comparison results. The user can verify some or all of the suggested corrections/updates as indicated in the presented explanation by, e.g., removing recorded codes that are deemed "incorrect" and including "correct" or "missing" billing codes in the medical record (step 48). The updated medical record can then be stored (step 53).

On the other hand, if the system is operating in "Auto Correction" mode (affirmative determination in step 46), the system will automatically generate an updated medical record based on the comparison results (step 49). If user verification of the update is not needed (negative determination in step 50), the system will automatically store the updated medical record (step 53). On the other hand, if user verification is needed (affirmative determination in step 50), the system can present the updated medical record to the user so that the user can review the proposed corrections/updates to the billing information (step 51). If user verification is obtained (affirmative determination in step 52), the system will automatically store the updated medical record (step 53). If user verification is not obtained (negative determination in step52), the system can fetch and present the corresponding explanation and comparison results (step 47) allowing the user to manually update or correct the medical record (step 48), based on the user's verification of the extraction and comparison results. The overall process can be repeated for all patient medical records in a given database (step 54).

Figure 6:
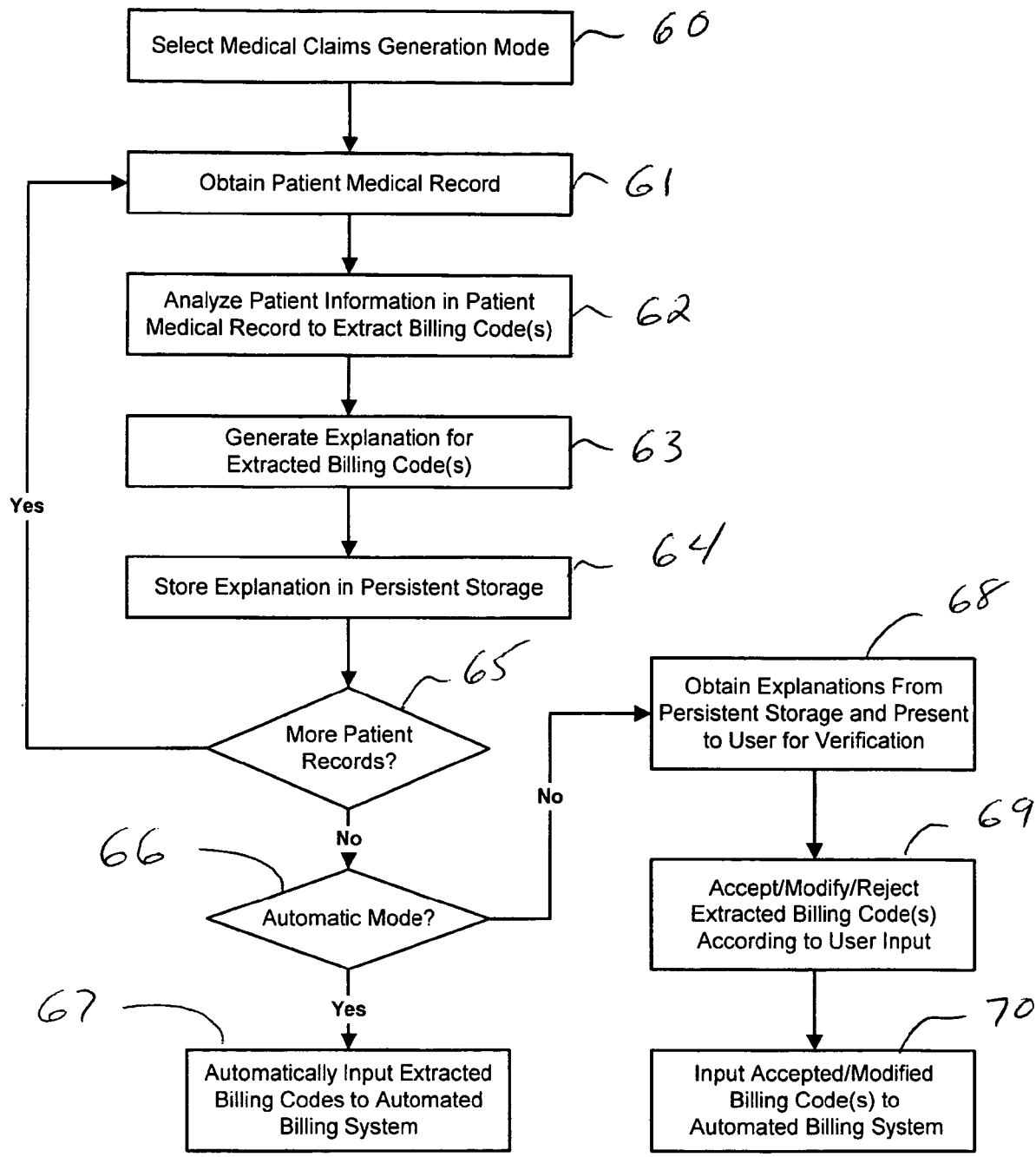
FIG. 6 is a flow diagram of a method for automatically extracting and processing billing information in patient medical records according to another exemplary embodiment of the invention.

FIG. 6 is a flow diagram that illustrates a method for automatically extracting and processing billing information in patient medical records for providing automated or semi-automated medical claims generation according to exemplary embodiments of the invention. When the user is granted authorized access to the system, the user can begin interaction by selecting a medical claims generation mode of operation (step 60). The user can submit a suitable query or command, which is received and processed by the system to commence processing of all patient medical records in a particular database and the system will begin accessing the patient medical record(s) (e.g., CPR) in accordance with the user query/command (step 61). For each patient medical record that is accessed (step 61), the system will automatically extract one or more billing codes from the medical record by analyzing the patient information in the medical record using domain-specific criteria (step 62). In particular, similar to the methods described above, in one exemplary embodiment of the invention, the process of extracting billing information comprises extracting all possible billing codes (including diagnosis codes and procedural codes) that are supported by the patient clinical information in the medical based on all domain-specific criteria in a domain knowledge base. In one exemplary embodiment of the invention, when performing automated extraction of billing information, the system does not consider or give significant weight to actual diagnosis codes or procedural codes recorded in the patient record as supporting evidence for billing information. However, depending on the domain-specific criteria, other codes related to medical procedures, resources, etc., may be defined as criteria for establishing a particular diagnosis. Next, the system can generate an explanation for the extracted billing information (step 63) and store the explanation persistently for subsequent access (step 64). The automated extraction process can be performed for all patient medical records in a database (step 65).

The claims generation mode may include an "auto mode", in which the system automatically generates a medical claim for billing using the extracted billing information from the patient medical record (step 67) (or the system sends the extracted billing information as input to a separate automated billing system). If the system is not operating in auto mode (negative determination in step 66), the system can fetch and present the corresponding explanation to the user (step 68) allowing the user to manually accept, reject or modify the extracted billing codes (step 69). In such instance, the extracted billing codes that are accepted or modified can be used for automatically generating a medical claim for the patient medical record (step 70).

It is to be appreciated that in another embodiment of the invention, the methods of FIGS. 5 and 6 can be combined such that an automated correction mode is performed to correct and update billing information in a patient medical record, whereby the billing codes of the updated/corrected medical record are automatically identified, extracted and used as input for automated claims generation.

Figure 7:
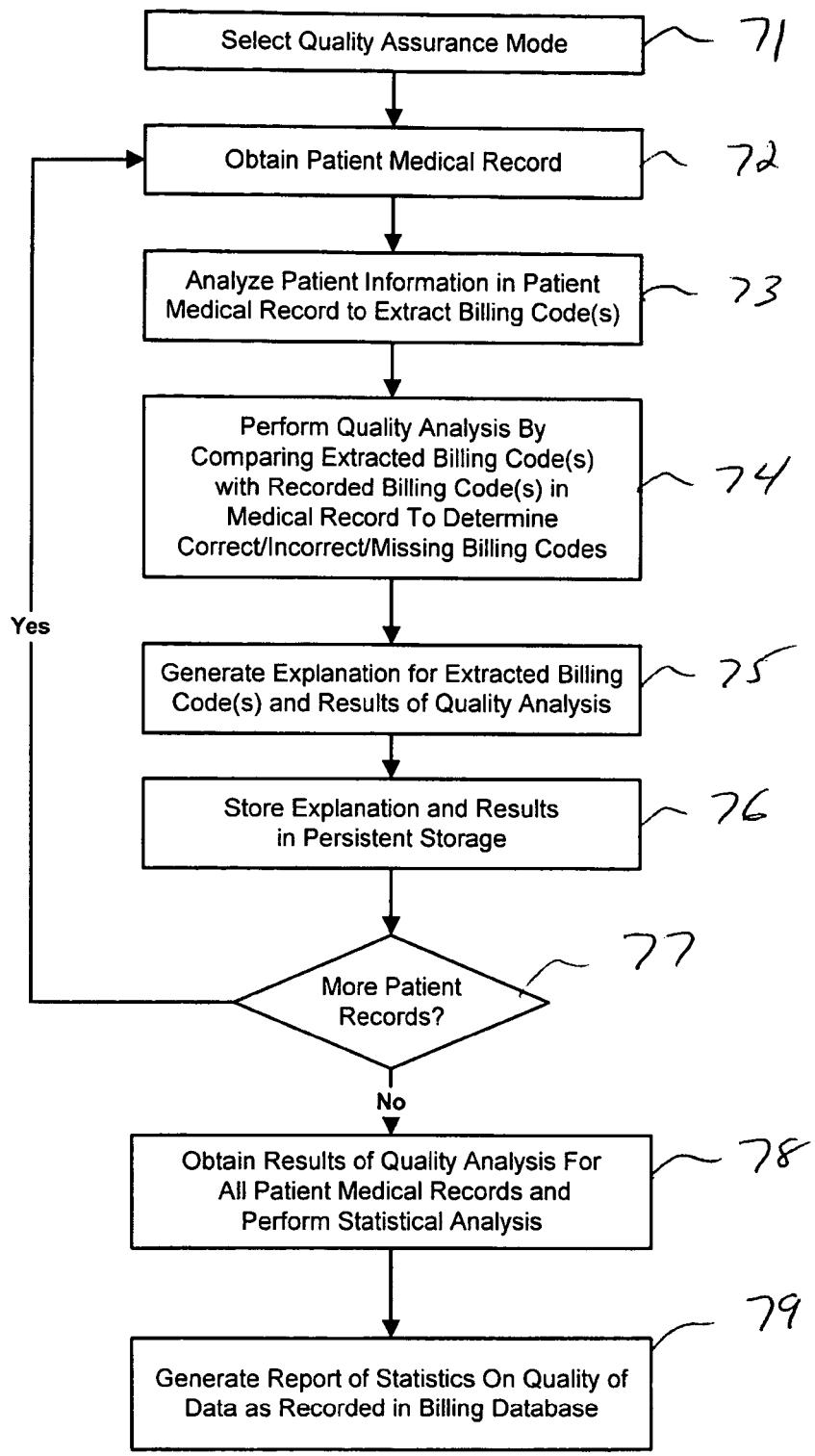
FIG. 7 is a flow diagram of a method for automatically extracting and processing billing information in patient medical records according to another exemplary embodiment of the invention.

FIG. 7 is a flow diagram that illustrates a method for automatically extracting and processing billing information in patient medical records for providing automated quality assurance of billing data as recorded in patient medical record databases, according to exemplary embodiments of the invention. More specifically, FIG. 7 illustrates a method for reporting statistics on the quality of billing data that is stored in medical billing databases according to an exemplary embodiment of the invention.

Referring to FIG. 7, when the user is granted authorized access to the system, the user can begin interaction by selecting an automated quality assurance mode of operation (step 71). The user can submit a suitable query or command, which is received and processed by the system to commence processing of all patient medical records in a particular database and the system will begin accessing the patient medical records in accordance with the user query/command (step 72). For each patient medical record that is accessed (step 72), similar to the extraction processes described above, the system automatically extracts all possible billing codes (including diagnosis codes and procedural codes) that are supported by the patient clinical information in the medical based on all domain-specific criteria in a domain knowledge base. In one exemplary embodiment of the invention, when performing automated extraction of billing information, the system does not consider or give significant weight to actual diagnosis codes or procedural codes recorded in the patient record as supporting evidence for billing information. However, depending on the domain-specific criteria, other codes related to medical procedures, resources, etc., may be defined as criteria for establishing a particular diagnosis.

Next, similar to the process (step 43) discussed above with reference to FIG. 5, the system will perform a quality analysis of the billing information recorded in the patient medical record by identifying (or otherwise extracting) the billing code(s) that are actually recorded in the patient medical record and comparing the recorded billing code(s) with the extracted billing code(s) to determine whether the recorded billing codes are "correct" or "incorrect" and/or determine if the patient medical record is "missing" billing code(s) that should be included (sep 74). More specifically, in one exemplary embodiment, a recorded billing code will be deemed "correct" and accepted if there is a corresponding extracted billing code based on the patient information (e.g., clinical information). Indeed, in such instance, the recorded billing code will be deemed acceptable as being supported by the patient information in the medical record based on relevant domain-specific criteria for such for such billing code. In addition, a recorded billing code will be deemed "incorrect" and rejected, if there is an extracted billing code that is contrary to the recorded billing code. Indeed, in such instance, the recorded billing code will be deemed unacceptable as not being supported by patient information in the medical record. Furthermore, a billing code will be deemed "missing", if the recorded billing codes in the patient medical record do not include an extracted billing code. Indeed, in such instance, the billing code is deemed missing as being supported by the patient information, but yet not included in the medical patient record.

The results of the comparison (in step 74) are used to assess the quality of the billing information (billing codes) as actually recorded in the medical record by collecting statistics regarding how many recorded billing codes were correct, incorrect, missing, etc. The system can generate an explanation for the extracted billing information, which can include the quality analysis results and the supporting basis for the missing, correct, incorrect codes (step 75), and store the explanation and quality analysis results persistently for subsequent access (as explained below) (step 76). This quality analysis process is performed for all patient medical records in a billing database (step 77).

When all the relevant patient medical records have been processed, the system will obtain all the quality analysis data that was collected and stored for each of the patient medical records and perform a statistical analysis to provide an indication of the quality of billing data as recorded in the billing database (step 78). The system will then generate a report of such statistical analysis (step 79). In one exemplary embodiment of the invention, the report can include the statistical data associated with the number of correct, incorrect and/or missing billing codes, as well as the results of any statistical analysis that can performed using such data to provide an indication or basis as to the quality of the recorded billing data in a database.

Figure 8:
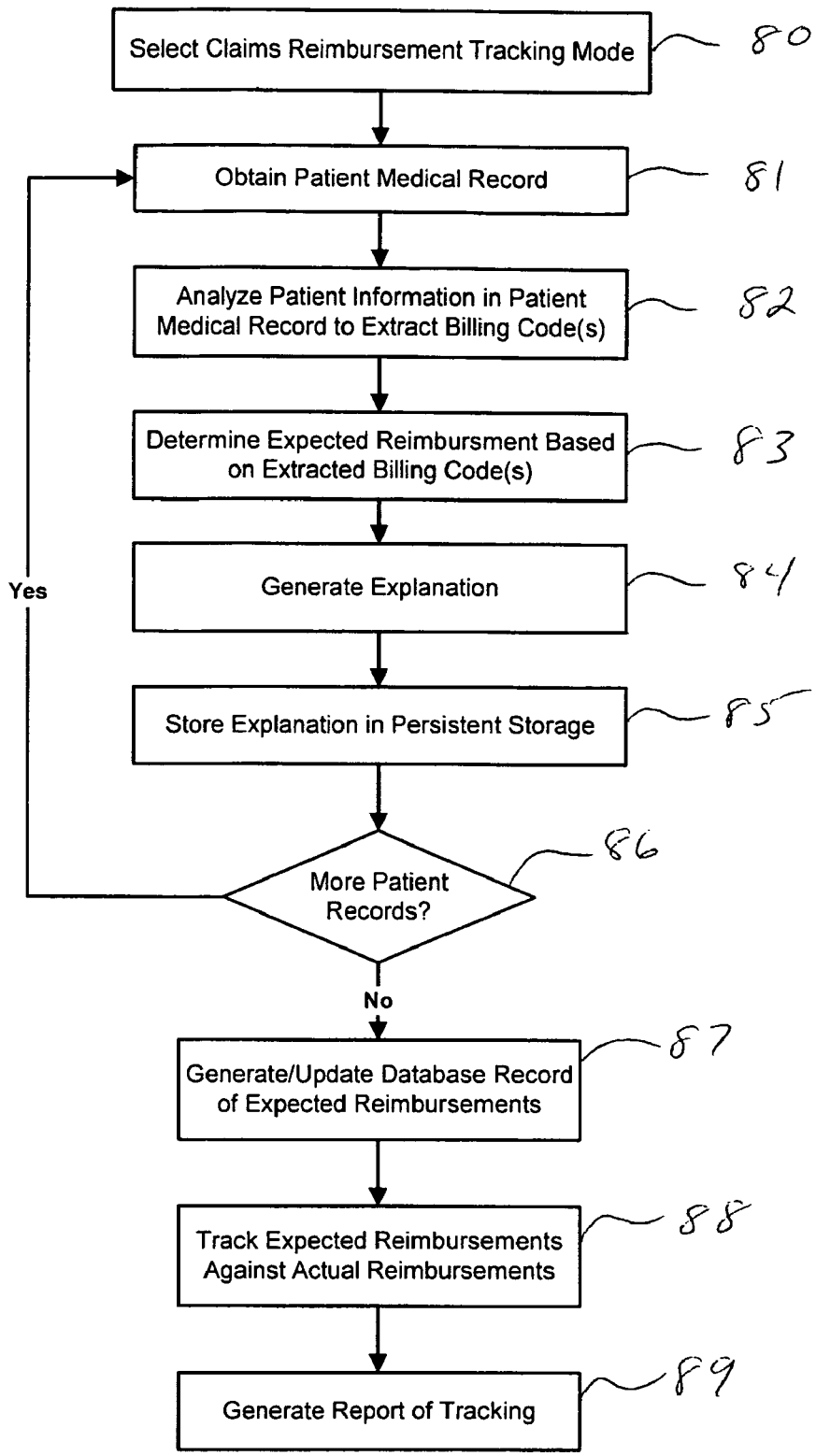
FIG. 8 is a flow diagram of a method for automatically extracting and processing billing information in patient medical records according to another exemplary embodiment of the invention.

FIG. 8 is a flow diagram that illustrates a method for automatically extracting and processing billing information in patient medical records for providing automated claims reimbursement tracking according to an exemplary embodiment of the invention. More specifically, FIG. 8 illustrates a method for automatically tracking expected medical claim reimbursements based on billing information in patient medical records against actual reimbursements received for purposes of medical accounting. Referring to FIG. 8, when the user is granted authorized access to the system, the user can begin interaction by selecting an automated claims tracking mode (step 80). The user can submit a suitable query or command, which is received and processed by the system to commence processing of all patient medical records in a particular database and the system will begin accessing the patient medical records in accordance with the user query/command (step 81).

For each patient medical record that is accessed (step 81), the system automatically extracts all recorded billing codes from the medical record (step 82). More specifically, in one exemplary embodiment of the invention, the validity/correctness/integrity of the billing codes as recorded in the medical record is presumed, such that the system identifies and extracts the billing codes that are recorded in the patient medical record. In this regard, the method of FIG. 8 can be an extension to the methods of FIGS. 5 or 6, wherein the recorded billing codes of the patient record have been previously assessed/verified/corrected/updated and are presumed to accurately reflect all possible billing information supported by the clinical data in the patient medical record.

Once the recorded billing codes of the patient medical record are extracted (step 82), the system can automatically determine an expected reimbursement based on the extracted billing information by determining the amount of medical reimbursements associated with each of the extracted billing codes (step 83) via a knowledge base of medical billing, for example. The system can generate an explanation of an expected reimbursement based on the extracted billing information and corresponding billing amounts associated therewith (step 84) and store the explanation persistently (step 85) for subsequent access. A determination as to an expected amount of medical billing reimbursement may further depend on whether or not clinical guidelines have been followed as specified by domain-specific criteria.

When all the medical records have been processed (affirmative result in step 86), the system can automatically generate a database record of expected reimbursements for all patient medical records in the database (step 87), wherein the record allows manual or automated entry of actual medical reimbursements received from an insurance company for each of the patient medical records, thereby allowing the system to automatically track the expected reimbursements against the received reimbursements for each patient (step 88). The system can periodically generate a report of such tracking (step 89) based on information maintained in the database records for purposes of medical billing accounting, etc.

It is to be appreciated that systems and methods according to the invention, which provide automated procedures for verifying the correctness of diagnoses or diagnosis codes included in electronic patient medical record databases and for automatically correcting/updating such diagnoses or diagnosis codes, can be effectively implemented for enhancing the value and quality of clinical data and patient records. Systems and methods according to the invention ensure higher quality patient data that can be used in automated systems that provide standardized assessment of care outcomes and processes, regulatory oversight of healthcare providers, medical billing and accurate calculation of fees or reimbursements, etc.

For example, the present invention can be implemented in conjunction with the systems and methods discussed in U.S. patent application Ser. No. 10/287,054, filed Nov. 4, 2002 entitled "Patient Data Mining for Automated Compliance" and U.S. patent application Ser. No. 10/287,074 filed on Nov. 4, 2002 entitled "Patient Data Mining for Quality Adherence", which are both commonly assigned and fully incorporated herein by reference.

U.S. patent application Ser. No. 10/287,074 describes a system and method for generating accurate quality adherence information during the course of patient treatment, which processes clinical data extracted from patient records against a guidelines knowledge base containing clinical guidelines, wherein a quality adherence engine monitors adherence with the clinical guidelines for the patients being treated based on the clinical data. In one embodiment, the present invention can be implemented for enhancing the quality of the patient clinical data to thereby provide a better assessment as to the adherence to clinical guidelines. The methods disclosed in this patent can be used for determining whether a patient's medical treatment as indicated in the patient's medical record has followed clinical guidelines according to domain-specific criteria.

U.S. patent application Ser. No. 10/287,054 discloses a system and method for automatically generating performance measurement information for health care organizations. Again, the present invention can be implemented in conjunction with such system for enhancing the quality of the patient clinical data that is used for generating performance measurements.

Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A method for processing medical information, comprising the steps of:
    obtaining a medical record of a patient, wherein the medical record comprises patient information from structured and unstructured data sources;
    analyzing with a computer the patient information from at least the unstructured data source in the medical record using domain-specific criteria; and
    automatically extracting billing information from the medical record as part of the analysis.

2. The method of claim 1, wherein extracting billing information comprises extracting one or more billing codes.

3. The method of claim 2, wherein the billing codes comprise a diagnosis code, a procedure code or both.

4. The method of claim 1, wherein the patient information comprises clinical information and financial information of the patient.

5. The method of claim 1, wherein extracting billing information comprises extracting all billing codes that are supported by the patient information based on all domain-specific criteria in a domain knowledge base.

6. The method of claim 1, wherein the domain-specific criteria comprises institution-specific domain knowledge.

7. The method of claim 6, wherein the institution-specific domain knowledge relates to one or more of data at a hospital, document structures at a hospital, policies of a hospital, guidelines of a hospital, and variations at a hospital.

8. The method of claim 1, wherein the domain-specific criteria includes condition-specific or disease-specific domain knowledge.

9. The method of claim 8, wherein the condition-specific or disease-specific domain knowledge includes one or more of factors that influence risk of a condition or disease, disease progression information, complications information, outcomes and variables related to a condition or disease, measurements related to a condition or disease, and policies and guidelines established by medical bodies.

10. The method of claim 1, further comprising generating an explanation that includes one or more pointers to relevant patient information, relevant domain-specific criteria, or relevant patient information and domain-specific criteria, which supports the extracted billing information.

11. The method of claim 10, further comprising presenting the explanation to a user for verifying the billing information.

12. The method of claim 1, further comprising automatically generating a medical claim for the patient using the extracted billing information.

13. The method of claim 1, further comprising:
presenting the extracted billing information to the user for verification; and
automatically generating a medical claim for the patient using the extracted billing information, if the extracted billing information is verified by the user.

14. The method of claim 13, further comprising:
modifying the extracted billing information in response to user input, if the billing information is not verified by the user; and
automatically generating a medical claim for the patient using the modified extracted billing information.

15. The method of claim 1, further comprising automatically updating the medical record of the patient using the extracted billing information.

16. The method of claim 15, wherein automatically updating the medical record comprises using the extracted billing information to (i) correct billing information in the medical record, which is determined to be incorrectly recorded in the medical record or (ii) insert billing information into the medical record, which is determined to be missing from the medical record.

17. The method of claim 15, further comprising presenting an updated medical record to a user for verification, wherein automatically updating the medical record of the patient is performed in the updated medical record is verified by the user.

18. The method of claim 1, further comprising:
(a) automatically assessing the quality of the patient information of the medical record using the extracted billing information to obtain quality assessment results; and
(b) storing the quality assessment results for the medical record.

19. The method of claim 18, further comprising performing steps (a) and (b) for a plurality of medical records in an electronic database; and
automatically generating quality assurance statistics based on the quality assessment results obtained for the plurality of medical records.

20. The method of claim 18, wherein the quality assessment results comprise information regarding occurrences of correct, incorrect and/or missing billing codes in the medical record.

21. The method of claim 1, further comprising automatically determining an expected amount of medical billing reimbursement based on the extracted billing information.

22. The method of claim 21, further comprising:
maintaining the expected amount in the medical record; and
reconciling the expected amount with an actual reimbursement received.

23. The method of claim 21, wherein determining an expected amount of medical billing reimbursement further depends on whether or not clinical guidelines have been followed as specified by domain-specific criteria.

24. The method of claim 10, wherein the explanation further comprises information as to whether or not clinical guidelines have been followed as specified by domain-specific criteria.

25. The method of claim 1 wherein automatically extracting comprises inferring a diagnosis and the associated billing information from the medical record.

26. The method of claim 25 wherein inferring comprises inferring the diagnosis and the associated billing information from the medical record without reference to diagnosis codes.

27. The method of claim 25 wherein inferring comprises determining a probability.

28. In a program storage device readable by a machine, tangibly embodying a program of instructions executable on the machine to perform steps for processing medical information, the program storage device comprising instructions for:
obtaining a medical record of a patient, wherein the medical record comprises patient information from structured and unstructured data sources;
analyzing the patient information from at least the unstructured data source in the medical record using domain-specific criteria; and
automatically extracting billing information from the medical record as part of the analysis.

29. The program storage device of claim 28, wherein the instructions for extracting billing information comprise instructions for extracting one or more billing codes.

30. The program storage device of claim 28, wherein the patient information comprises clinical information and financial information of the patient.

31. The program storage device of claim 28, wherein the instructions for extracting billing information comprise instructions for extracting all billing codes that are supported by the patient information based on all domain-specific criteria in a domain knowledge base.

* * * * *